United States Patent [19]

Hihara et al.

[11] 4,102,348
[45] Jul. 25, 1978

[54] LOW FREQUENCY MEDICAL TREATMENT APPARATUS

[75] Inventors: Sokichi Hihara, Yokohama; Mikio Horiuchi; Takeshi Ohe, both of Tokyo, all of Japan

[73] Assignee: Kabushiki Kaisha Nippon Coinco, Tokyo, Japan

[21] Appl. No.: 796,512

[22] Filed: May 13, 1977

[30] Foreign Application Priority Data

May 19, 1976 [JP] Japan .................................. 51-56687

[51] Int. Cl.² ............................................. A61N 1/36
[52] U.S. Cl. ................................ 128/422; 128/2.1 P; 128/404
[58] Field of Search .................. 128/421, 422, 423 R, 128/2.1 P, 417, 418, 404, 405

[56] References Cited
U.S. PATENT DOCUMENTS

| | | | |
|---|---|---|---|
| 2,447,127 | 8/1948 | Landaver | 128/417 |
| 2,823,311 | 2/1958 | Bastir | 128/421 |
| 2,823,678 | 2/1958 | Luftman et al. | 128/422 |
| 3,185,939 | 5/1965 | Moss et al. | 128/422 |
| 3,241,557 | 3/1966 | Masaki | 128/422 |
| 3,516,413 | 6/1970 | McDonald et al. | 128/422 |
| 3,645,267 | 2/1972 | Hagfors | 128/421 |
| 3,886,932 | 6/1975 | Suessmilch | 128/2.1 P |
| 4,068,669 | 1/1978 | Niemi | 128/2.1 P |

*Primary Examiner*—William E. Kamm
*Attorney, Agent, or Firm*—Koda and Androlia

[57] ABSTRACT

A low frequency medical treatment apparatus comprising an over-current preventing measure with an over-current detecting circuit and a switching circuit to control an output transmission path according to the detection output, a shock preventing measure having a control circuit for opening or closing an output wave transmission path in response to a switching element whose operating state is changed depending on whether or not an output controller is set at its minimum set position, and a measure of improving comfortability in use having a circuit for controlling the output wave transmission upon contact of a touching element with human body and a circuit for maintaining the output waveform unchanged.

5 Claims, 10 Drawing Figures

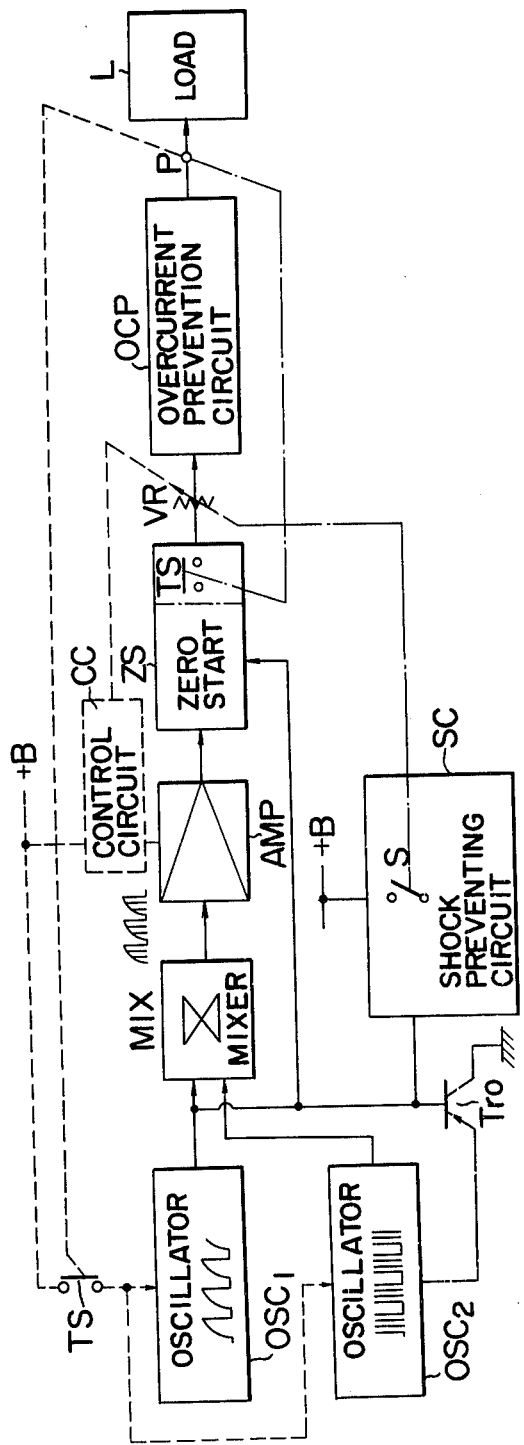
F I G. 1
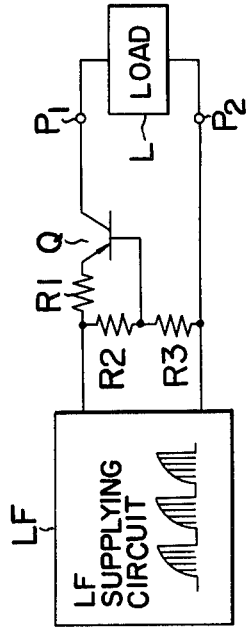
F I G. 2(b)
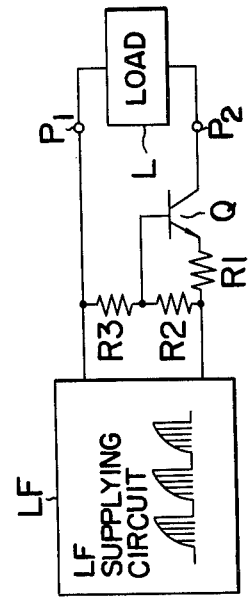
F I G. 2(a)

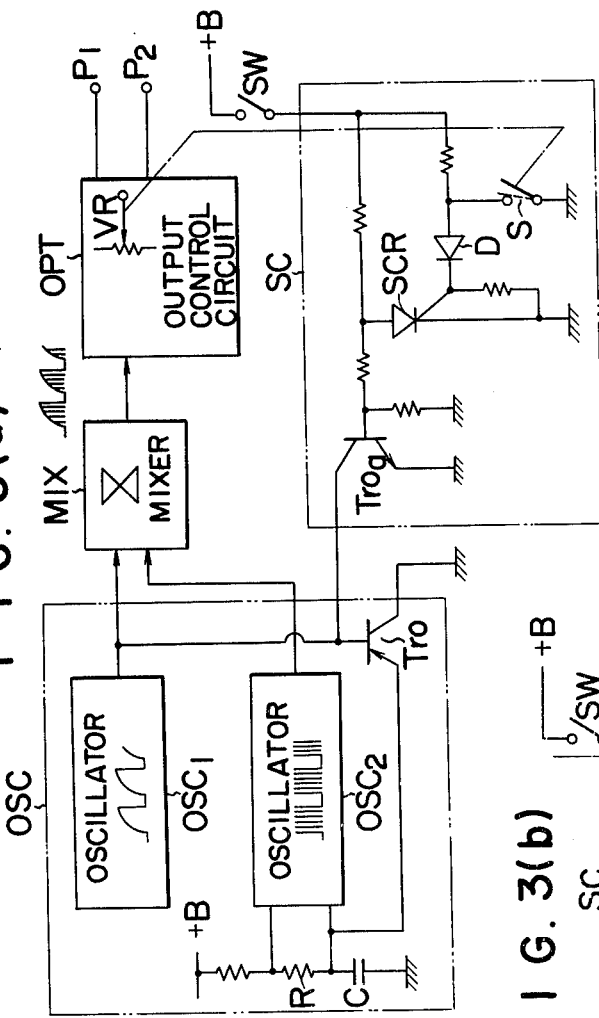
F I G. 3(a)
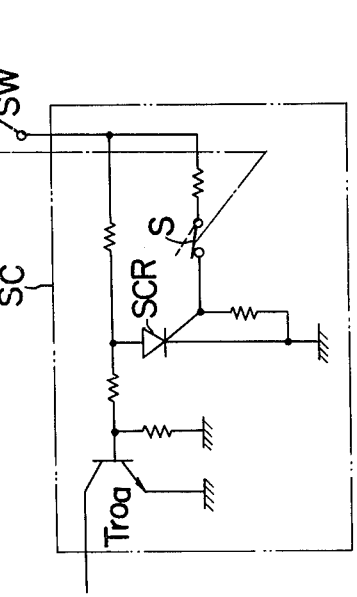
F I G. 3(b)

ENERGIZE
PAUSE

LOW FREQUENCY MEDICAL TREATMENT APPARATUS

BACKGROUND OF THE INVENTION

This invention relates to low frequency medical treatment apparatuses in which a low frequency current is allowed to flow through the human body to carry out medical treatment, and more particularly to a circuitry for operating the apparatus securely and comfortably.

Known in the art is a low frequency medical treatment apparatus which carries out medical treatment by applying an electrical output of relatively low voltage and low frequency to necessary portions of the human body on the basis of the phenomenon that upon application of electric current to the human body, especially to a muscle, the muscle is vibrated.

In the medical treatment apparatus of this type, many safety measures of securely applying electric current are required. The safety measures are, for instance, to prevent the flow of excessively large current, and to prevent shocks caused by application of a large electric power to the human body. A variety of circuits have been proposed as the safety measures. However, these conventional circuits are still disadvantageous in responding characteristics and cost.

On the other hand, the medical treatment apparatus of this type is frequently used, and its medical treatment effects are remarkable. Therefore, it should be taken into consideration whether it can be used comfortably. However, in the conventional medical treatment apparatus mentioned above, measures taken to meet such requirements are not always sufficient and satisfactory.

SUMMARY OF THE INVENTION

Accordingly, an object of this invention is to provide a low frequency medical treatment apparatus in which all of the above-described drawbacks accompanying conventional low frequency medical treatment apparatuses have been eliminated.

More specifically, an object of the invention is to provide a low frequency medical treatment apparatus in which a security measure of preventing the application of over-current or shock to the human body, and a measure of permitting a comfortable use of the apparatus.

The foregoing object and other objects of this invention have been achieved by the provision of a low frequency medical treatment apparatus which is provided with: (1) an over-current preventing circuit, as an over-current preventing measure, comprising an over-current detecting circuit, and a semiconductor switching circuit which selectively opens and closes an output wave transmission path in response to the output of the detecting circuit; (2) a shock preventing circuit, as a shock preventing measure, comprising a switching element whose operating state is changed depending on whether or not an output controller is set at its minimum set position, and a control circuit for opening or closing the output wave transmission path in response to the operation of the switching element; and (3) means, as a measure of improving comfortability in use, comprising a circuit for controlling the transmission of the output wave upon contact of a touching element with the human body, and a circuit for maintaining the waveform of the output wave unchanged.

The nature, principle and utility of this invention will become more apparent from the following detailed description and the appended claims when read in conjunction with the accompanying drawings, in which like parts are designated by like reference characters.

BRIEF DESCRIPTION OF THE DRAWINGS

In the accompanying drawings:

FIG. 1 is a block diagram illustrating the whole arrangement of a low frequency medical treatment apparatus according to this invention;

FIG. 2(a) and FIG. 2(b) are diagrams showing examples of an over-current preventing circuit shown in FIG. 1;

FIGS. 3(a) and 3(b) are diagrams showing examples of a shock preventing circuit shown in FIG. 1;

DETAILED DESCRIPTION OF THE INVENTION

Figure 4:
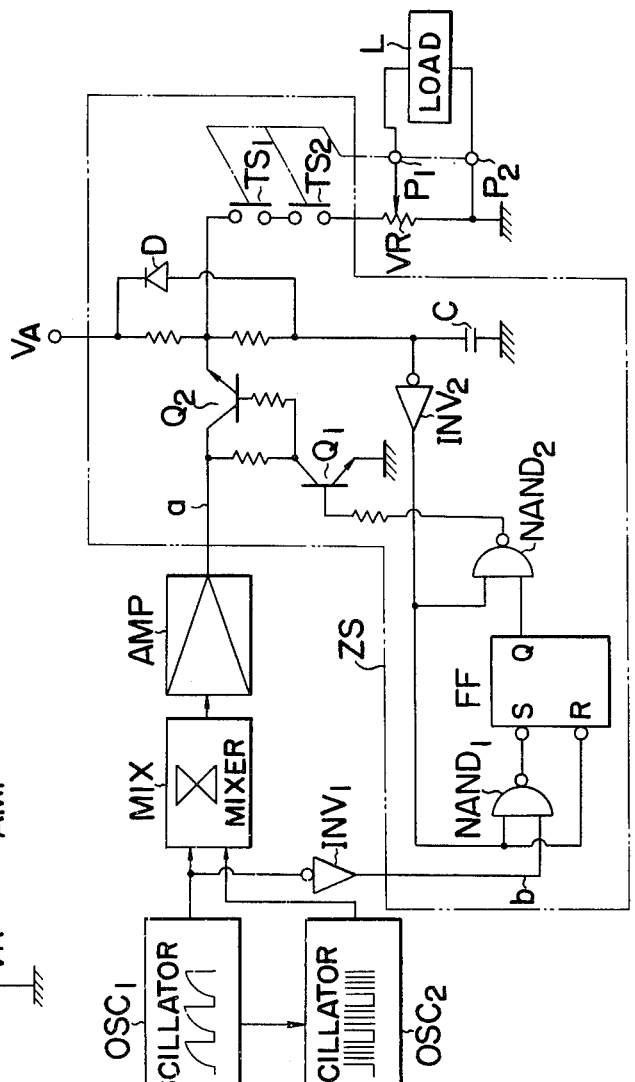
FIGS. 4 and 5 are diagram illustrating examples of a zero start circuit shown in FIG. 1.

One example of a low-frequency medical treatment apparatus according to the invention is briefly shown in FIG. 1. Its component circuits are shown in FIGS. 2 to 7 in detail.

The apparatus, as shown in FIG. 1, comprises a modulating wave oscillator $OSC_1$ for generating a modulating wave of the order of 1 Hz whose rising form is moderate, and a fundamental-wave oscillator $OSC_2$ for generating a pulse wave whose frequency is several times as high as the frequency of the modulated wave. The outputs of these oscillators $OSC_1$ and $OSC_2$ are applied to a mixer circuit MIX. The oscillator $OSC_2$ is in synchronization with the oscillator $OSC_1$ by means of a transistor $Tr_o$. Therefore, the modulating wave and the fundamental wave are generated in synchronization and are applied to the mixer circuit MIX. The mixer circuit MIX is an AND circuit operating in an analog mode, and serves to mix these waves. The waves thus mixed, or a mixed wave, are applied through an amplifier AMP to a zero start circuit ZS.

Under the condition that during the output pause period of the modulated wave oscillator $OSC_1$, a touching element through which the mixed wave is applied directly to the human body is in contact with the human body and a touch switch TS is closed, the zero start circuit ZS operates to introduce the output of the amplifier AMP to an output controller VR, thereby to improve comfortability in use.

The output controller VR has the same functions as those of a variable resistor with a switch. When the output controller is at its minimum set position, the switch S is opened (or closed), and its open (or closed) output is applied to a shock preventing circuit SC. If, in the case where the apparatus has been energized, the output controller VR is set at the minimum set position once, the shock preventing circuits operate to allow the oscillators $OSC_1$ and $OSC_2$ to perform the synchronization operation with the aid of the transistor $Tr_o$; while if the output controller VR is not brought to be set at the minimum set position, the shock preventing circuit SC operates to block the synchronization operation.

The output from the output controller VR is delivered to an over-current preventing circuit OCP which serves to prevent the output current from becoming excessively large. The output of the over-current preventing circuit OCP is applied through its output terminal P to a load L, or the human body.

Two more functions (indicated by broken lines in FIG. 1) may be added to those of the medical treatment apparatus. One of the two functions is that when the touching element is brought into contact with the human body, a touch switch TS is closed to start the operations of the oscillators $OSC_1$ and $OSC_2$. The other is that when after the apparatus has been energized, the output controller VR is brought to be set at the minimum set position, and the amplifying operation of the amplifier AMP is controlled by a control circuit CC operating with the output controller VR. The former can carry out an operation similar to that of the zero start circuit ZS, while the latter can carry out an operation similar to that of the shock preventing circuit SC.

The component circuits of the apparatus will be described with reference to FIGS. 2 to 7.

Shown in FIGS. 2(a) and 2(b) are examples of the over-current preventing circuit OCP.

In FIG. 2(a), reference character LF designates a low-frequency supplying source of the apparatus. The low-frequency supplying source LF serves to produce an output wave obtained by mixing a modulating wave of the order of 1 Hz which rises moderately and a pulsive fundamental wave whose frequency is several times as high as that of the modulating wave. This output wave is applied to the load L through the touching element comprising electrodes $P_1$ and $P_2$ to be connected to the human body. Between the low-frequency supplying circuit LF and the electrodes $P_1$ and $P_2$ there is provided a current limiter circuit comprising an NPN type transistor Q and resistors $R_1$, $R_2$ and $R_3$ defining the voltage and current conditions thereof.

Consider that the electrodes $P_1$ and $P_2$ are almost in a short-circuited state. In this case, as the collector-emitter circuit of the transistor Q allows the flow of a large current, the voltage drop across the emitter resistor $R_1$ is considerably increased, and therefore the potential of the emitter is positive and high in level. In this connection, a divided voltage by the resistors $R_2$ and $R_3$ is applied to the base of the transistor Q. In the case of over-current under the condition that the voltage is not changed as in the case of shorting the electrodes $P_1$ and $P_2$, the emitter potential is raised higher than the base potential. Accordingly, the transistor Q is reversely biased, and the conduction between the collector and the emitter of the transistor Q is interrupted. As a result, the flow of the over-current is stopped.

Shown in FIG. 2(b) is another example of the over-current preventing circuit OCP, in which a PNP type transistor Q is employed. In this case, of course, the conductive directions between the base and the emitter, and between the collector and the emitter of the transistor Q are opposite to those in the case of FIG. 2(a). And the voltage conditions are so determined as to meet the requirements for the PNP transistors. The other conditions for the circuit in FIG. 2(b) are the same as those in FIG. 2(a).

Shown in FIG. 3(a) is one example of the shock preventing circuit SC. In FIG. 3(a), reference character OSC designates an oscillation circuit comprising the modulating-wave oscillator $OSC_1$, the fundamental-wave oscillator $OSC_2$, and a synchronization circuit for synchronizing these oscillators $OSC_1$ and $OSC_2$. The oscillation circuits OSC operates to shychronously generate the modulating wave and the fundamental wave. These two waves thus synchronously generated are applied to the mixer circuit MIX where these waves are mixed.

The mixer circuit MIX is an AND circuit performing analog operation, for instance. When both of the modulating wave and the fundamental wave are positive, the mixer circuit MIX produce a positive output whose level is in accordance with the level relation between these two waves. On the other hand, if one of the two waves is at the zero level, the mixer circuit MIX provides a zero level output. The mixer circuit MIX produces an output wave in intermittent state in which the fundamental wave changes its level with the modulating wave as its envelope. This output wave is applied to an output control circuit OPT where the output wave is controlled by the output controller VR. As a result, an output defined by the control of the output controller are provided across the output terminals $P_1$ and $P_2$.

In FIG. 3(a), reference character SC is intended to designate a control circuit operating to permit or inhibit the production of the output of oscillator circuit OSC according to whether or not the output controller VR in the output control circuit OPT is set at the minimum set position. In this control circuit, a gate signal is applied or not applied to a thyrister separately according to opening or closing of a switch S which is similar to a switch provided for a variable resister, as a result of which the thyristor is rendered conductive or non-conductive, and a transistor $Tr_{oa}$ is rendered conductive or non-conductive, thereby stopping or allowing the production of the output from the oscillator circuit.

The operation of the above-described circuit will be described. Consider that when a power switch SW is turned on, the output controller VR is set at its minimum set position and the switch S is open. In this case, a firing signal is applied to the gate of the thyristor SCR, to turn on the same SCR. As a result, the base potential of the transistor $Tr_{oa}$ is brought to the zero volt, and the transistor $Tr_{oa}$ is rendered non-conductive. As a result, in the oscillator OSC, when the foundamental wave is positive, the transistor $Tr_o$ is rendered non-conductive; and when the foundamental wave is at the zero level, the transistor $Tr_o$ is rendered conductive. And when the transistor $Tr_o$ is conductive, a capacitor C in the time constant circuit of the fundamental-wave oscillator $OSC_2$ is shorted; and when the transistor $Tr_o$ is non-conductive, the capacitor C is released. Accordingly, the fundamental wave oscillator $OSC_2$ starts its oscillation when the modulating wave is positive, and it suspends the oscillation when the modulating wave is at the zero level. That is, the transistor $Tr_o$ serves to cause the oscillators $OSC_1$ and $OSC_2$ to carry out the synchronization operation. The synchronously generated modulating wave and fundamental wave are applied to the mixer circuit MIX, and an output wave to meet the AND condition is produced to be applied to the output control circuit OPT. In this operation, the output controller VR in the output control circuit OPT has been set at the minimum set position, and therefore no output is introduced to the output terminals $P_1$ and $P_2$. Then, the output controller VR is set to increase the output. As a result, the switch S is closed, and the firing signal is no longer applied to the gate of the thyristor SCR. However, since the thyristor SCR has a function of self-holding, it remains conductive, and therefore the transistor $Tr_o$ is maintained non-conductive. Therefore, the oscillator circuit OSC continues applying the output waves to the mixer circuit, while the output control circuit OPT applies an output corresponding to the set value of the output controller VR to the output terminals $P_1$ and $P_2$.

On the other hand, in the case where, when the power switch SW is turned on, the output controller VR has been set at a position other than the minimum set position; as the switch S has been closed, no firing signal is applied to the gate of the thyristor SCR, and therefore the thyristor SCR is not turned on. Accordingly, as long as the power switch SW is closed, a high level voltage is applied to the base of the transistor $Tr_{oa}$ to render the same conductive. As a result, the level of the base of the transistor $Tr_o$ in the oscillator circuit OSC is changed to the zero level to render the transistor $Tr_o$ conductive. Thus, similarly as in the case of the transistor $Tr_{oa}$, as long as the power switch SW is closed, the transistor $Tr_o$ is kept conductive.

Therefore, the capacitor C in the time constant circuit of the oscillator circuit $OSC_2$ is maintained short-circuited, and therefore no fundamental wave is produced by the oscillator circuit $OSC_2$. Therefore, only the modulating wave is applied to the mixer circuit MIX, and therefore the necessary AND conditions are not established therein. Thus, the mixer circuit MIX provides no output wave. In order to provide the output wave, it is necessary to set the output controller VR of the output control circuit OPT at the minimum set position once, and to open the switch S.

Shown in FIG. 3(b) is another example of the control circuit SC. In this example, the switch S is so designed that when the output controller VR is set at the minimum set position, the switch S is closed; and when the output controller VR is brought to set at a position where a maximum output is provided from the minimum set position, the switch S is opened. In addition, if the switch S is closed, then a firing signal is applied to the gate of the thyristor SCR; however, if the switch S is opened, no firing signal is applied to the gate of the thyristor SCR. The operations of the control circuit SC are similar to those of the control circuit SC in FIG. 3(a) except for the operation of the switch S described above.

In the examples described above, the output of the control circuit is applied to the oscillation circuit to control the latter; however, it is possible to control the mixer circuit by the output. Furthermore, in the oscillation circuit the synchronous generation of the modulating wave and the fundamental wave may be employed.

In addition, in the above-described examples the switch of the variable resistor is employed as the switching element responding to whether or not the output control is set at the minimum set position; however, this switch may be replaced by another element, such as a combination of a level detector for detecting an output level of the output control circuit and a switching circuit responding to the operation of the level detector.

Shown in FIG. 4 is a power control circuit provided for the above-described control circuit CC, and oscillators $OSC_1$ and $OSC_2$.

This circuit has the same object and effect as those of the shock preventing preventing circuits shown in FIGS. 3(a) and 3(b). In FIG. 4, reference characters $OSC_1$ and $OSC_2$ are a modulating-wave oscillator and a fundamental-wave oscillator, respectively, the output waves of which are applied to the mixer circuit MIX. The mixer circuit MIX provides the fundamental wave which has been modulated with the modulating wave as its envelope. The output wave from the mixer circuit MIX is applied to the output controller VR where it is modified to have a desired level. The output wave thus modified is applied through the amplifier AMP and the output terminals $P_1$ and $P_2$ to the load (or the human body) L.

In FIG. 4, the output controller VR of the control circuit CC is a variable resistor with a switch S. When the output controller VR is set at the minimum set position, then the switch S is closed to turn on the thyristor SCR to energize the amplifier AMP. In addition, the touch element is provided with a touch response switch TS. When the touching element is brought into contact with the load L, the oscillators $OSC_1$ and $OSC_2$ are energized through the switch TS; however, when it is detached from the load, these oscillators are deenergized.

The operation of the circuit shown in FIG. 4 will be described.

It is assumed that the power is applied and the touching element is in contact with the human body. In this case, the touch response switch TS is closed, and the power supply +B is applied to the oscillators $OSC_1$ and $OSC_2$. Accordingly, the oscillator $OSC_1$ provides a modulating wave, and the oscillator $OSC_2$ produces a fundamental wave while the modulating wave is at a predetermined level.

The modulating wave and the fundamental wave are applied to the mixer circuit MIX, which forms a mixed wave. The mixed wave is applied through the output controller VR to the amplifier AMP. In this case, if the output controller VR is set at the minimum set position, the switch S is closed. As a result, the thyristor SCR is rendered conductive to energize the amplifier AMP. The thyristor SCR has a function of self-holding. Therefore, even if the switch S is opened by adjusting the output controller VR thereafter, the amplifier AMP is maintained energized.

On the other hand, if the output controller VR is not set at the minimum set position, the switch S is opened as was described. Therefore, before the output controller VR is set at the minimum set position, the amplifier AMP is not energized. As a result, no output wave is provided at the touching element.

If the touching element is detached from the human body, then the touch response switch TS is opened to suspend the energization of the oscillators $OSC_1$ and $OSC_2$. Accordingly, the production of the modulating wave and the fundamental waves respectively by the oscillators $OSC_1$ and $OSC_2$ is also suspended. Thus, regardless of the operations of the mixer circuit MIX and the circuits at the rear stage thereof, no output wave is introduced to the touching element.

In the circuit described above, the power supply circuit for the oscillators $OSC_1$ and $OSC_2$ is opened by means of the touch response switch TS which is operated when the touching element brought into contact with the human body is disconnected from the human body. This circuit may be replaced by any circuit if it allows the oscillation circuit to start its operation when the touching element is brought into contact with the human body. Furthermore, in the above-described circuit, the switch S operating in response to the setting of the output controller VR is so designed as to close at the minimum set position, so that the firing signal is applied to the thyristor SCR. However, the circuit may be so designed that the switch is opened when the output controller VR is set at the minimum set position, so as to apply a firing signal to the thyristor. In addition, the circuit may be so designed that the thyristor SCR can control each or all of the mixer circuit and the oscillator except the amplifier.

Figure 5:
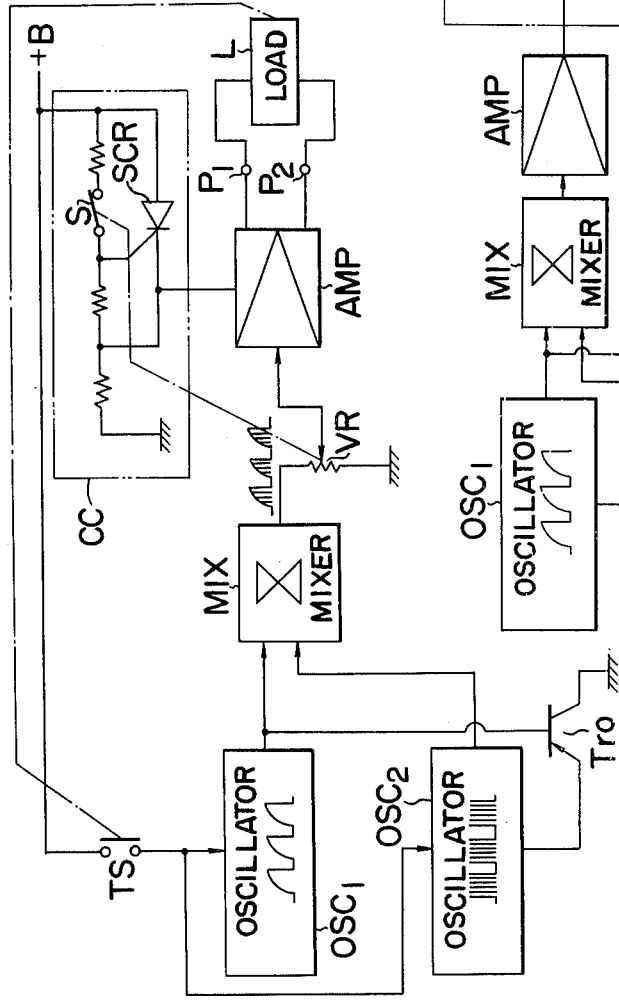

FIG. 5 is a block diagram illustrating an example of the above described zero start circuit ZS, in which reference characters $OSC_1$ and $OSC_2$ designate respectively a modulating wave oscillator and a fundamental wave oscillator, the outputs of which are applied to the mixer circuit MIX, where a mixed wave is produced from these outputs and is applied to the amplifier AMP. The output thus amplified is applied to the output controller VR through the zero-start circuit ZS and touch response switches $TS_1$ and $TS_2$ provided respectively for the two electrodes. As a result, the output wave is applied to the load (or the human body) through the touching element from the output terminals $P_1$ and $P_2$ connected to the output controller VR. Thus, the zero start circuit ZS operates to control the output of the amplifier AMP in response to the output of the oscillator $OSC_1$ and the on-off operation of the touch response switch TS, thereby to provide for the load an output whose waveform is such that it rises from the zero level.

Figure 6A:
FIGS. 6(a) and 6(b) are waveform diagrams for a description of the circuit shown in FIG. 5.
Figure 6B:
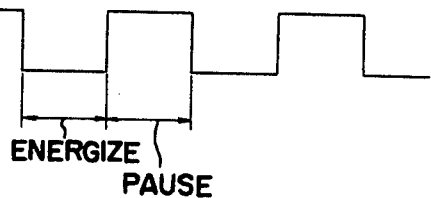

FIGS. 6(a) and 6(b) show respectively the output of the amplifier AMP and the output of the oscillator $OSC_1$ which have been passed through the inverter $INV_1$ in FIG. 5. By utilizing these waveform diagrams, the operation of the circuit shown in FIG. 5 will be described.

Consider that the touching element is in contact with the human body, the touch response switches $TS_1$ and $TS_2$ are closed, and the oscillators $OSC_1$ and $OSC_2$ produce the outputs. In this case, the mixer circuit MIX mixes the outputs of the oscillators $OSC_1$ and $OSC_2$, and the output of the mixer MIX is applied to the amplifier AMP where it is amplified. The output thus amplified is applied to the collector of a transistor $Q_2$ in a output control circuit OCC. The transistor $Q_2$ responds to the operation of a transistor $Q_1$. The transistor $Q_1$ responds to the output of a NAND circuit $NAND_2$ due to the operations of a NAND circuit $NAND_1$, a flip-flop FF and the NAND circuit $NAND_2$.

Consider that the output of the oscillator OSC is at the zero level. In this case, the output of the inverter $INV_1$ is at the high level, and one input of the NAND circuit $NAND_1$ is at the high level. And, the circuit constants are so selected that, when the touch response switch TS is closed, the emitter of the transistor $Q_2$ is substantially at the ground level. Therefore, the input of the inverter $INV_2$ is substantially at the ground level, and the output of the same $INV_2$ is at the high level. Thus, the two inputs of the NAND circuit $NAND_1$ are at the high level, and its output is at the low level, thereby to set the flip-flop FF to provide an output at its output terminal Q. This output is applied to one input of the NAND circuit $NAND_2$. In this operation, as the high level output has been applied to the other input of the NAND circuit $NAND_2$, the output level of the NAND circuit $NAND_2$ is lowered to the low level, thereby to render the transistor $Q_1$ non-conductive. Accordingly, the transistor $Q_2$ introduces the output of the amplifier AMP to the load L through the touch response switch TS and the output controller VR.

On the other hand, in the case when the touch response switch TS is open, the input of the inverter $INV_2$ is at the high level, and its output is at the low level. Therefore, the NAND circuit $NAND_1$ provides the high level output, and the flip-flop FF is therefore not set. As the low level output of the inverter $INV_2$ is applied to the reset terminal R of the flip-flop FF to reset the same, the low level output is applied to the NAND circuit $NAND_2$ through the terminal Q. Accordingly, the NAND circuit $NAND_2$ applies the high level output to the transistor $Q_1$ to render the same conductive. As a result, the transistor $Q_2$ is rendered non-conductive, thereby preventing application of the output of the amplifier to the load L.

As was described above, the flip-flop FF is reset when the touch response switch TS is opened. This reset is carried out immediately after the touch response switch TS is opened. Therefore, even in the case also when the touch response switch TS which has been maintained closed is opened, the power supply to the load L is suspended immediately when the switch TS is opened.

In contrast, in the case when the touch response switch TS which has been maintained open is closed, the setting of the flip-flot FF is carried out after the output of the oscillator $OSC_1$ rises, and therefore the application of the output of the amplifier to the load is not immediately effected after the closure of the switch TS, thus preventing the human body from the electrical shock.

In this circuit, when the transistor $Q_2$ is conductive and the output of the amplifier AMP is applied to the load L, the emitter potential of the transistor $Q_2$ becomes the high level periodically, similarly as in the case of the output of the oscillator $OSC_2$. If this high level potential is applied, as it is, to the inverter $INV_2$, the flip-flop FF will be reset. In order to overcome this trouble, pulse components are removed from the high level potential by the use of the capacitor C. Furthermore, if the capacitor C is deteriorated to lose its capacitance, a considerably high voltage may be applied to the inverter $INV_2$. In order to prevent this, there is provided a diode D as shown in FIG. 5. In adition, if the amplifier AMP is provided with a transformer, a negative output may be produced due to undershoot. In this case, in order to protect the transistor $Q_2$ from damage, a reverse current preventing diode (not shown) may be connected in series to the emitter of the transistor $Q_2$.

In the example described above, two touch response switches are provided. However, this switch arrangement may be replaced by one touch response switch or three touch response switches in AND connection depending on the construction of the touching element.

For instance, in the case where the touching element comprises a ring-shaped electrode, and a center electrode disposed in the center of the ring-shaped electrode, the ring-shaped electrode may be provided with several switches which are connected in OR logic and are further connected to the center electrode in AND logic. In addition, in the above description, the oscillators $OSC_1$ and $OSC_2$ are operated synchronously; however, these oscillators may be operated independently. But, in this case, the rise of the mixed wave becomes irregular.

Figure 7:
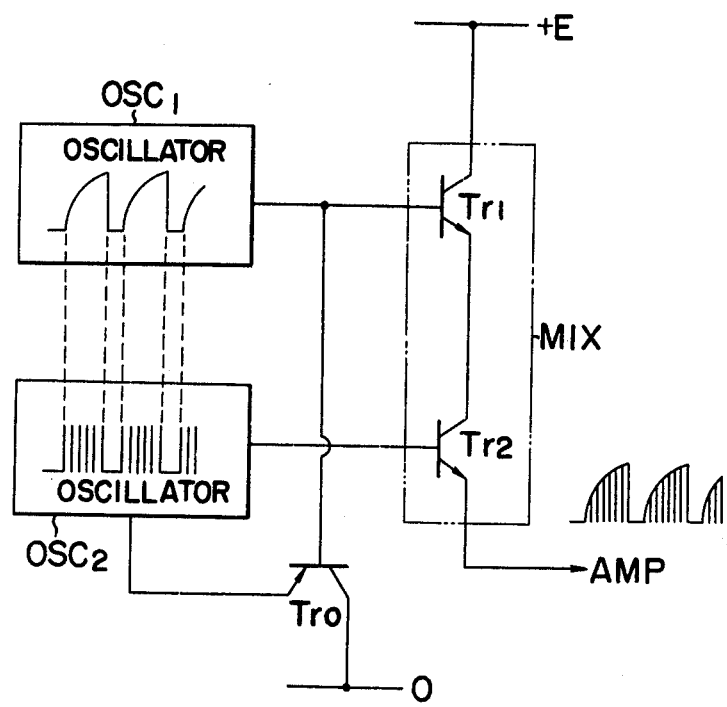
FIG. 7 is a diagram illustrating an example of a mixer circuit shown in FIG. 1.

FIG. 7 shows one example of the mixer circuit MIX. In FIG. 7, the outputs of the modulating wave oscillator $OSC_1$ and the fundamental wave oscillator $OSC_2$ are applied to transistors $Tr_1$ and $Tr_2$ forming an AND circuit. The output of the oscillator $OSC_1$ is applied to a transistor $Tr_o$ which is used to control the operation of the fundamental wave oscillator $OSC_2$ so that the operation of the oscillator $OSC_2$ follows that of the oscillator $OSC_1$. The transistor $Tr_o$ may be connected to any circuit point of the oscillator $OSC_2$, if its operation can be suspended by the conduction of the transistor. For instance, the transistor $Tr_o$ can be connected in series to the capacitor in a capacitor-resistor (CR) time constant circuit.

In operation, the modulating wave oscillator $OSC_1$ produces a modulating wave, which is applied to the transistor $Tr_o$ and $Tr_1$. As a result, whenever the modulating wave rises, the transistor $Tr_o$ is rendered conductive, thus starting the fundamental wave oscillator $OSC_2$; while when modulating wave falls (or decays), the transistor $Tr_o$ is rendered non-conductive, thus stopping the oscillator $OSC_2$. In other words, for the period of time of from the rise to the decay of the modulating wave, the fundamental wave oscillator $OSC_2$ provides its output, which is applied to the transistor $Tr_2$.

In consequence, when the modulating wave applied to the transistor $Tr_1$ by the oscillator $OSC_1$ rises, the fundamental wave is produced by the oscillator $OSC_2$ and is applied to the transistor $Tr_2$. In contrast, when the modulating wave decays, the production of the fundamental wave is suspended. Thus, the modulating wave and the fundamental wave are, in a synchronization mode, applied to the transistors $Tr_1$ and $Tr_2$, respectively. Accordingly, at the emitter of the transistor $Tr_2$ an analogous mixed wave of the modulating wave and the fundamental wave is provided, and yet the phase relationship of these two waves are maintained unchanged at all times.

As is apparent from the above description, the medical treatment apparatus of this invention is provided with: (1) the over-current preventing circuit, as an over-current preventing measure, comprising the over-current detecting circuit, and the semiconductor switching circuit which selectively opens and closes the output wave transmission path in response to the output of the detecting circuit; (2) the shock preventing circuit, as a shock preventing measure, comprising the switching element whose operating state is changed depending on whether or not the output controller is set at its minimum set position, and the control circuit for opening or closing the output wave transmission path in response to the operation of the switching element; and (3) means, as a measure of improving comfortability in use, comprising a circuit for controlling the transmission of the output wave upon contact of the conductive element with the human body and a circuit for maintaining the waveform of the output wave unchanged. Thus, the medical treatment apparatus provided by the invention is protected by safety means which is low in cost and positive in operation. In addition, the medical treatment apparatus can be used comfortably.

We claim:

1. A low frequency medical treatment apparatus for applying through a touching element to the human body a medical treatment wave obtained by mixing a modulating wave of low frequency and fundamental wave of higher frequency than that of the modulating wave, which apparatus comprising:
    (a) oscillating means for synchronously generating a modulating wave which rises relatively moderately and decays relatively abruptly, and after a pause interval rises moderately again, and a pulsive fundamental wave whose frequency is higher than that of said modulating wave;
    (b) mixing means connected to said oscillating means, for mixing said modulating wave and fundamental wave generated by said oscillating means to produce a mixed wave;
    (c) zero start means for delivering the mixed wave starting at the zero level thereof under conditions that said modulating wave is in a pause interval and said touching element is in contact with the human body;
    (d) output control means for controlling a level of said mixed wave according to a setting operating thereof, said output control means having a switch which is turned on or off depending on whether or not said output control means is set at its minimum set position;
    (e) shock preventing means for controlling at least one of paths of said modulating wave, fundamental wave and transmission mixed wave so that when said output control means is set at the minimum set position, said switch of said output control means is operated to deliver said mixed wave; and
    (f) over-current preventing means operatively connected to said touching means for preventing a flow of excessive mixed wave in said touching element.

2. An apparatus as claimed in claim 1, in which said oscillating means comprises synchronizing means for synchronizing said modulating wave and said fundamental wave.

3. An apparatus as claimed in claim 1, in which said shock preventing means comprises a first switching means operatively connected between said synchronizing means and said output control means, said first switching means being operated in response to operation of said switch of said output control means to control said synchronizing means thereby to control provision of said mixed wave.

4. An apparatus as claimed in claim 1, which further comprises amplifier means connected between said output control means and said touching element, for amplifying the mixed wave and delivering same to said touching element, and amplfiier control means which becomes operative with operation of said switch of said output control means to control said amplifier, and in which said touching element is provided with a touch response switch which is connected to said oscillating means, said touch response switch being operated when said touching element is brought into contact with the human body, to control said oscillating means.

5. An apparatus as claimed in claim 1, in which said over-current preventing means comprises in combination switching means through which said mixed wave is allowed to be delivered to said touching element, and current limiting means connected to said switching means to control current and voltage conditions of said switching means, thereby to prevent a flow of excessive current in said touching element.

* * * * *